United States Patent
Morin et al.

(10) Patent No.: US 7,263,446 B2
(45) Date of Patent: Aug. 28, 2007

(54) STRUCTURAL HEALTH MANAGEMENT SYSTEM AND METHOD FOR ENHANCING AVAILABILITY AND INTEGRITY IN THE STRUCTURAL HEALTH MANAGEMENT SYSTEM

(75) Inventors: Brent A. Morin, Cave Creek, AZ (US); Joseph J. Nutaro, Phoenix, AZ (US); Nicholas J. Wilt, Glendale, AZ (US); Steven R. Thompson, Phoenix, AZ (US)

(73) Assignee: Honeywell International, Inc., Morristown, NJ (US)

( * ) Notice: Subject to any disclaimer, the term of this patent is extended or adjusted under 35 U.S.C. 154(b) by 26 days.

(21) Appl. No.: 10/976,748

(22) Filed: Oct. 29, 2004

(65) Prior Publication Data

US 2006/0106550 A1 May 18, 2006

(51) Int. Cl.
*G01B 3/00* (2006.01)
*G01B 5/00* (2006.01)
*G06F 19/00* (2006.01)

(52) U.S. Cl. ............................ 702/34; 702/33; 702/35; 702/36

(58) Field of Classification Search .................... 702/34
See application file for complete search history.

(56) References Cited

U.S. PATENT DOCUMENTS

| | | | |
|---|---|---|---|
| 4,419,900 A | 12/1983 | Scott et al. | |
| 5,184,516 A | 2/1993 | Blazic et al. | |
| 5,383,133 A | 1/1995 | Staple | |
| 5,774,376 A | 6/1998 | Manning | |
| 6,006,163 A | 12/1999 | Lichtenwalner et al. | |
| 6,076,405 A | 6/2000 | Schoess | |
| 6,192,759 B1 | 2/2001 | Schoess | |
| 6,370,964 B1 | 4/2002 | Chang et al. | |
| 6,396,262 B2 | 5/2002 | Light et al. | |
| 6,594,590 B2* | 7/2003 | Woods et al. ................. | 702/35 |
| 2001/0022514 A1 | 9/2001 | Light et al. | |
| 2001/0047691 A1 | 12/2001 | Dzenis | |
| 2002/0154029 A1 | 10/2002 | Watters et al. | |
| 2003/0009300 A1* | 1/2003 | Giurgiutiu ................... | 702/35 |
| 2003/0167141 A1 | 9/2003 | Staszewski | |
| 2003/0233876 A1 | 12/2003 | Huang et al. | |

FOREIGN PATENT DOCUMENTS

| | | |
|---|---|---|
| EP | 0 067 531 A2 | 12/1982 |
| WO | WO 00/64737 | 11/2000 |
| WO | WO 02/062206 A2 | 8/2002 |
| WO | WO 03/106958 A2 | 12/2003 |

\* cited by examiner

*Primary Examiner*—John Barlow
*Assistant Examiner*—Sujoy Kundu
(74) *Attorney, Agent, or Firm*—Ingrassia, Fisher & Lorenz

(57) ABSTRACT

A structural health management system is disclosed. The structural health management system comprises a zone of sensors. A first sensor data collector is coupled to a first subset of the sensors in the zone; and a second sensor data collector coupled to a second subset of the sensors in the zone. In the present invention, loss of a sensor data collector does not result in the loss of ability to perform nondestructive testing in an entire zone.

33 Claims, 5 Drawing Sheets

STRUCTURAL HEALTH MANAGEMENT SYSTEM AND METHOD FOR ENHANCING AVAILABILITY AND INTEGRITY IN THE STRUCTURAL HEALTH MANAGEMENT SYSTEM

TECHNICAL FIELD

This invention relates to the field of structural health management, and, more specifically, to a method for improving integrity for a structural health management system.

BACKGROUND

Nondestructive testing is a procedure for determining the quality or characteristics of a structure without permanently altering the structure or the structure's properties. Examples include ultrasonic and radiographic inspection. In the avionics field, nondestructive evaluations of airplane components are done to insure the structural integrity of the airplane. In typical nondestructive testing schemes, a certified inspector performs one or more nondestructive tests at the aircraft. This process may be repeated at regular intervals to monitor the structural health of the aircraft.

While this type of nondestructive testing scheme can be effective, it has several drawbacks. First, the test typically needs to be conducted by trained inspectors, which can incur significant costs, including the potential loss of operational revenue, when having an inspector perform the tests on site. Second, to enable efficient analysis and repetitive comparison over time, a non-subjective decision process driven by inspection data, inspection method parameters, location, decision criteria, and material properties within the context of the structure being inspected may be required. Current inspection approaches may not preserve these necessary components. Although each inspection can be analyzed individually, a collection of inspections may not be analyzed in toto.

To resolve some of the drawbacks of current nondestructive schemes, other structural health management schemes have been developed. In one structural health management technique, ultrasonic transducers can be placed, for example, on the fuselage of the aircraft to be tested. The ultrasonic transducers are then coupled to an onboard testing computer. The testing computer can be used to run nondestructive tests when needed by using the installed ultrasonic transducers.

The above-described system allows for nondestructive testing to be done without having an inspector bring equipment to the aircraft. Additionally, the automated inspection and determination of the state of the inspected material preserves accurate location data, as well as the associated data used to perform the inspection and make the determination. This allows multiple self-referential inspections of an area over an extended period of time, enabling correlation, trending and other sophisticated analysis of the inspection data across vehicles and over time.

In complex systems, multiple sensors may be required. These sensors provide data directly to a processor for analysis. A drawback to this arrangement is that for a system with many sensors, the amount of wiring can be very large. This is a particular concern when the system is deployed in an environment where the weight of the excess wiring can have a detrimental effect. What is needed is a structural health management system that reduces the amount of wiring and enhances the availability and integrity of the system.

BRIEF SUMMARY

In one embodiment a structural health management system is disclosed. In the system, a plurality of sensors are mounted on a to be tested material, such as an aircraft. The sensors are arranged in zones of adjacent sensors. The system further comprises one or more sensor data collectors, wherein each sensor data collector is coupled to sensors from at least two zones. This increases the availability of the system as the loss of a sensor data collector does not result in the loss of ability to perform nondestructive testing in an entire zone.

In a second embodiment of the present invention, a method for connecting a plurality of sensors in a zone of sensors to sensor data collectors is provided. In the method, a first subset of the plurality of sensors is coupled to a first sensor data collector; and a second subset of the plurality of sensors is coupled to a second sensor data collector.

In another embodiment, ultrasonic pulses are generated with the plurality of sensors to produce ultrasonic waves; the waves, as influenced by any internal structure are received at the plurality of sensors as data; the data is collected at the first sensor data collector and the second sensor data collector; the data is sent to a processor; and the data is evaluated at the processor to determine if there is any damage.

In another embodiment data collected by a first subset of sensors in a zone is sent to a first sensor data collector and data from a second subset of sensors in a zone is sent to a second sensor data collector. The data from the first sensor data collector and the second sensor data collector is sent to a processor. The processor compares the data from the first subset of sensors and from the second subset of sensors. If the data differs by more than a predetermined threshold, then a possible error condition exists. The error could be in the sensors, the sensor data collectors or the wiring between the sensors and the sensor data collectors. This helps to increase the integrity of the system because detecting faults in the system helps avoid possible faulty or erroneous test results.

BRIEF DESCRIPTION OF THE DRAWINGS

The present invention will hereinafter be described in conjunction with the following drawing figures, wherein like numerals denote like elements, and.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description. While the invention is disclosed in an avionics embodiment, the teachings of the present invention are applicable to many different fields of endeavor.

Figure 1:
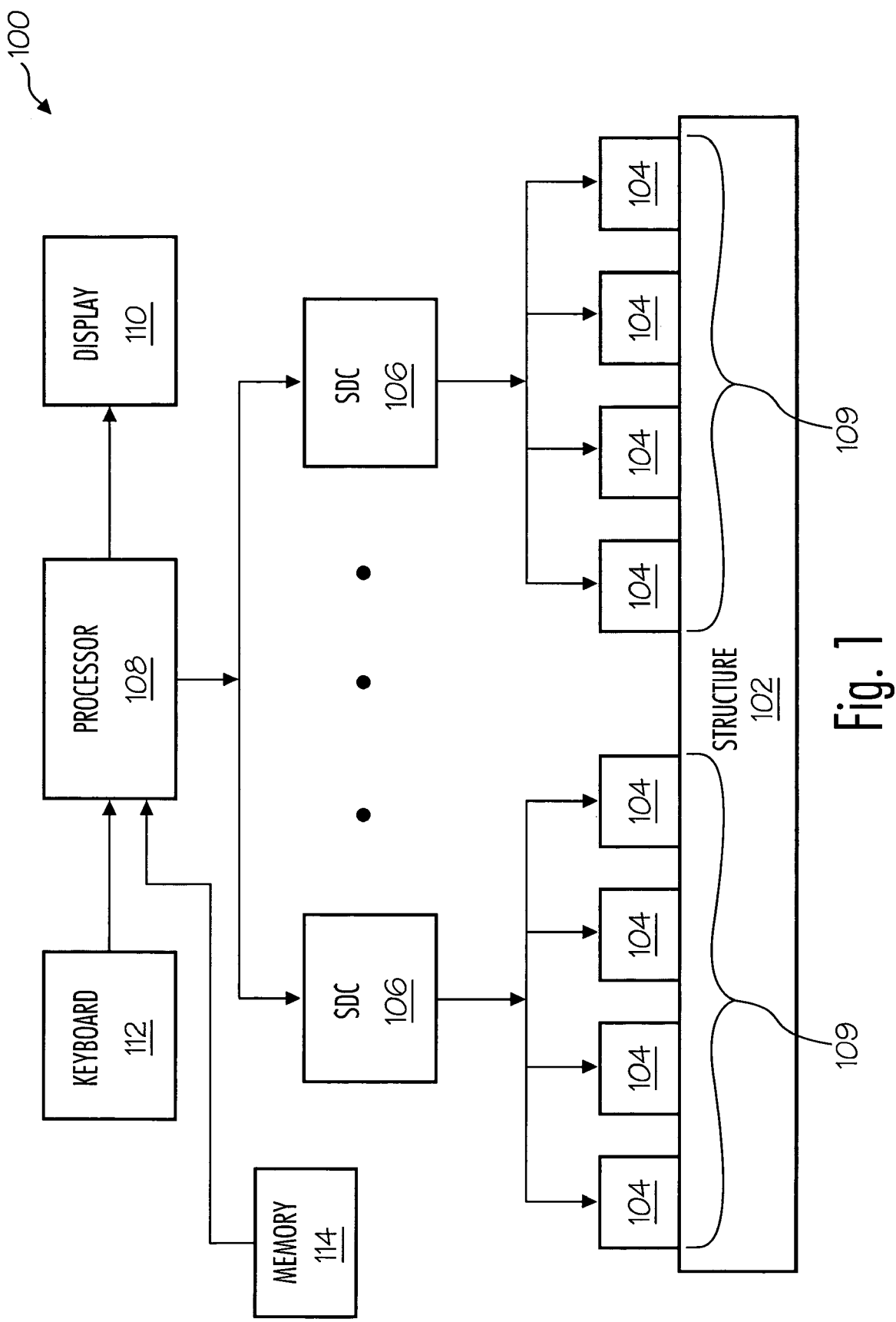
FIG. 1 illustrates an exemplary structural health mounting system in accordance with the teachings of the present invention.

FIG. 1 illustrates an exemplary structural health management system 100 in accordance with the teachings of the present invention. Structural health management system 100 includes a plurality of sensors 104 coupled to one or more sensor data collectors 106. Each sensor 104 is mounted to a structure 102 to be tested. In one embodiment, the sensors 104 are grouped as one or more zones 109 of sensors. The output of all the sensor data collectors 106 are provided as an input to at least one structural health monitoring processor 108. Various inputs and outputs can be provided to structural health monitoring processor 108. For example, processor 108 can be coupled to various input/output devices including a display 110, a keyboard 112 and the like. Processor 108 can also be coupled to a memory 114.

Sensors 104 can be ultrasonic transducers that convert electrical signals into mechanical vibrations and mechanical vibrations into electrical signals. Typically, sensor 104 converts electricity into mechanical vibrations that propagate waves in the structure 102 to which the sensor 104 is coupled via elastic deformation (this type of wave is known as an elastic wave). The propagated waves interact with various features within the structure 102 such as flaws or defects. The sensors 104 receive transmitted and reflected waves and convert the mechanical vibrations caused by these waves into electrical signals. These electrical signals can then be analyzed to determine if there are any flaws or defects in the structure 102.

The amount of time it takes for a wave to travel between two sensed locations is known as the time-of-flight. In addition to time-of-flight, signal amplitude and signal energy (as represented by the area under the rectified voltage curve) can be used in models to predict the underlying damage state of the area traversed by the propagated elastic waves. Various features within the structure 102, such as fatigue cracks or other structural flaws, can be identified and located based on these values obtained from data collected by the sensors 104.

While many different designs for sensors 104 exist, in one embodiment of the present invention, sensor 104 is a piezoelectric transducer. Piezoelectric transducers produce mechanical vibrations when an electric signal is applied and produce electrical signals when receiving mechanical vibrations. Typically, piezoelectric transducer uses piezoelectric ceramics that can be engineered to produce different wave modes.

Different types of waves induced by piezoelectric transducers can be used in nondestructive testing. In an embodiment of the present invention, the sensors 104 produce Lamb waves in structure 102. Lamb waves propagate throughout the entire thickness of plate-like structures, such as the composite material used for the skin of an aircraft. Lamb waves are a form of guided elastic waves distinct from the bulk waves used in traditional ultrasonic approach. Lamb waves traverse along the plate-like structure while exciting material throughout the plate's thickness. As a consequence, the use of Lamb waves allows distributed sensors schemes can be devised to examine the composite plate-like structure over a given area without the need to scan the transducers over certain areas.

Sensor data collectors (SDCs) 106, in one embodiment of the present invention, collect data from the sensors 104 in the form of electrical signals and send the data to processor 108 for evaluation. In another embodiment, sensor data collectors 106 collect data and can perform some analysis on the data prior to sending the data to the processor 108. By providing multiple sensor data collectors 106, if one sensor data collector 106 was to fail, the entire structural health management system 100 would not fail. Additionally, in one embodiment SDCs 106 accept multiple sensor inputs and provide a single high speed data output, multiple SDCs 106 resulting in a reduction of wiring required between the sensors 104 and the processor 108. Of course, SDCs 106 could provide multiple outputs to a processor, but, in a preferred embodiment, the SDCs 106 have fewer outputs to the processor 108 than inputs for sensors 104.

Processor 108 can be any device that can receive data from the sensor data collectors 106 and process the data to find or to help find flaws or defects in the structure 102. Processor 108 can be a commercial off the shelf processor and can include any components necessary to allow processor 108 to process the data, including memory, storage and the like. Various testing algorithms can also be run on processor 108. Processor 108 can couple to input/output devices such as the display 110, such as a CRT or LCD display, that displays information to a user.

Structure 102 can be any one of numerous types of material of interest to be tested. In one embodiment, structure 102 is a composite material used for the skin of an aircraft. In one exemplary embodiment, structure 102 is a, plate-like composite material such as the material used in to form modern aircraft skin.

Figure 2:
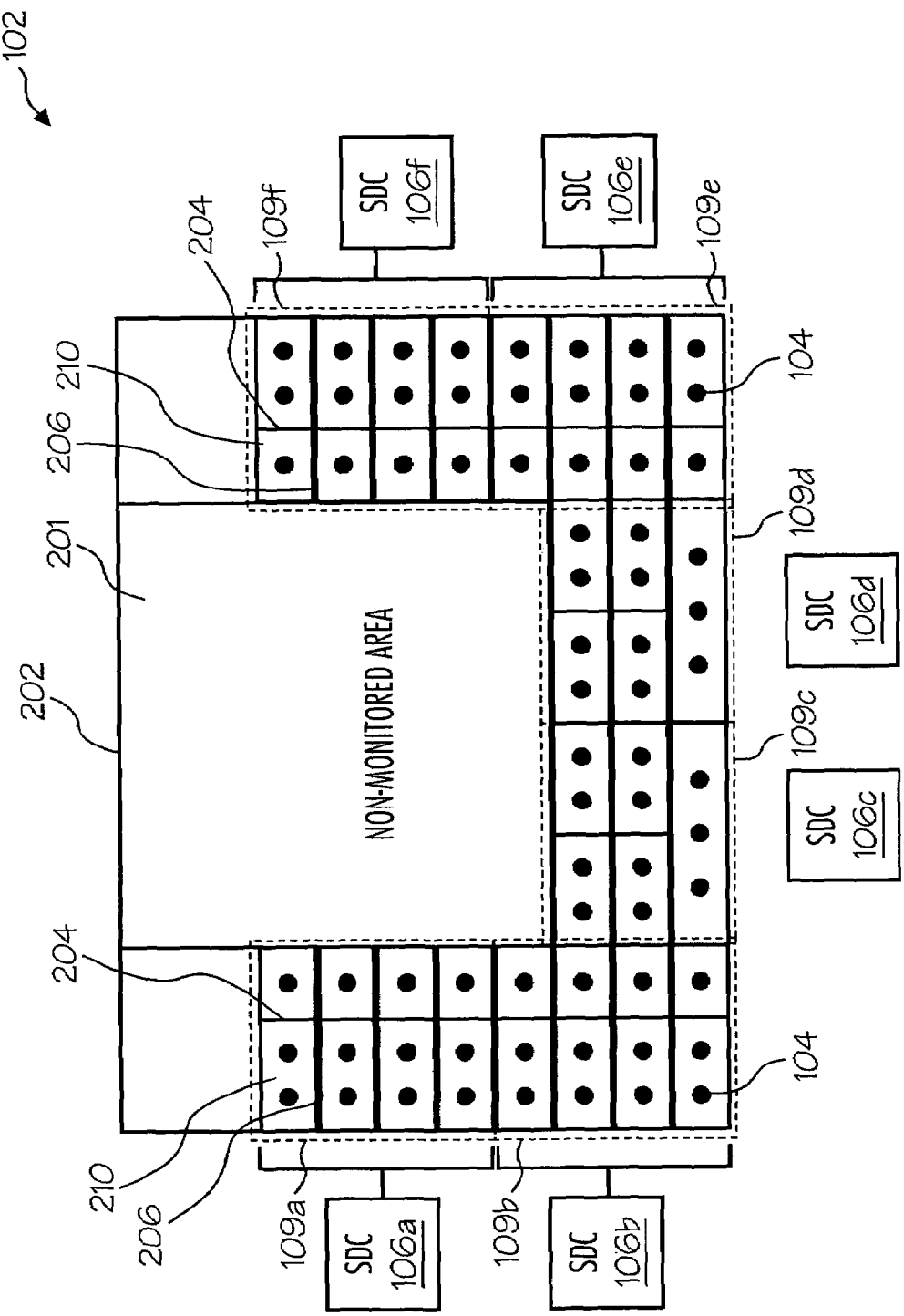
FIG. 2 illustrates the placement of sensors around a non-monitored area of an aircraft in accordance with the teachings of the present invention.

An exemplary arrangement of the sensors 104 and SDCs 106 as deployed in a structural health monitoring system 100 is illustrated in FIG. 2. To avoid unnecessarily complicating FIG. 2, SDCs 106 are illustrated as associated with a grouping of sensors in FIG. 2. As better viewed in FIG. 1, each sensor 104 will be coupled to one of the SDCs 106. FIG. 2 illustrates an exemplary section of structure 102 to be tested. As shown in FIG. 2, one or more sensors 104 are placed on the inside surface 202 of the structure 102 in sections 210 bordered by a pair of stringer members 206 and a pair of frame members 204. In the embodiment of FIG. 2, the structure 102 is adjacent to a non-monitored area 201. Non-monitored area 201 can be any area not monitored by the system 100 and, in an avionics embodiment where the structure 102 is aircraft skin, the non-monitored area 201 can be a structure such as a window, door and the like. As noted, FIG. 2 illustrates the inside surface 202 of the structure 102; the outside of the structure 102 is not visible in this perspective.

In operation, each sensor 104 can produce transmit and receive elastic wave energy. The elastic wave energy, produce by a sensor 104 converting mechanical energy to an elastic wave, can manifest itself in a variety of forms such as transient Lamb Waves, bulk waves, Raleigh waves and the like. These elastic waves can be transmitted, reflected, refracted, mode converted and attenuated as the elastic waves propagate through out the structure, interacting with internal features. As discussed previously, characteristics of any defect can be determined, in part, from the time-of-flight, signal amplitude, and signal energy (area under the rectified voltage curve) of the propagated elastic waves as received by a sensor. Additionally, the time of flight between sensors or between the start of an elastic wave and its return from reflection of a boundary can be used to determine distances between sensors and between sensors and boundaries.

In the embodiment illustrated in FIG. 2, sensors 104 are grouped into zones 109a-109b of adjacent sensors 104 and all the sensors 104 of the same zone are coupled to the same SDC 106. That is, a zone 109 of sensors 104, in one embodiment, is a collection of adjacent sensors 104. The number of sensors 104 in a zone 109 can vary at least in part, by the number of sensors 104 to which the SDC 106 can couple. As seen in FIG. 2, first SDC 106a couples to the sensors 104 in first zone 109a, second SDC 106b couples to the sensors 104 in second zone 109b, third SDC 106c couples to the sensors in third zone 109c, fourth SDC 106d couples to the sensors 104 in fourth zone 109d, fifth SDC 106e couples to the sensors 104 in fifth zone 109e, and sixth SDC 106f couples to the sensors 104 in sixth zone 109f. This arrangement helps to reduce the amount of wiring in a system 100 by requiring only a single wire from each SDC 106 to the processor 108.

While this arrangement of sensors 104 and SDCs 106 provides the ability to perform nondestructive testing, a failure of one SDC 106 will result in the loss of the ability to perform any nondestructive testing in the associated zone 109, due to the loss of the availability of sensors 104. To avoid the loss of ability to perform nondestructive testing in a given zone 109, in a second embodiment of the present invention the sensors 104 within a particular zone 109 are associated with at least two different SDCs 106. Alternatively, one SDC 106 can be coupled to sensors 104 from at least two different zones 109. In this embodiment, the group of sensors 104 need not be the same size as long as there are at least two groups with one or more sensors 104. Therefore, in this alternative embodiment, the loss of one SDC 106 will not result in the loss of the ability to receive data from all the sensors 104 in a given zone 109 since some of the sensors 104 wilt be coupled to a second SDC 106, increasing the availability of the system 100.

Figure 3:
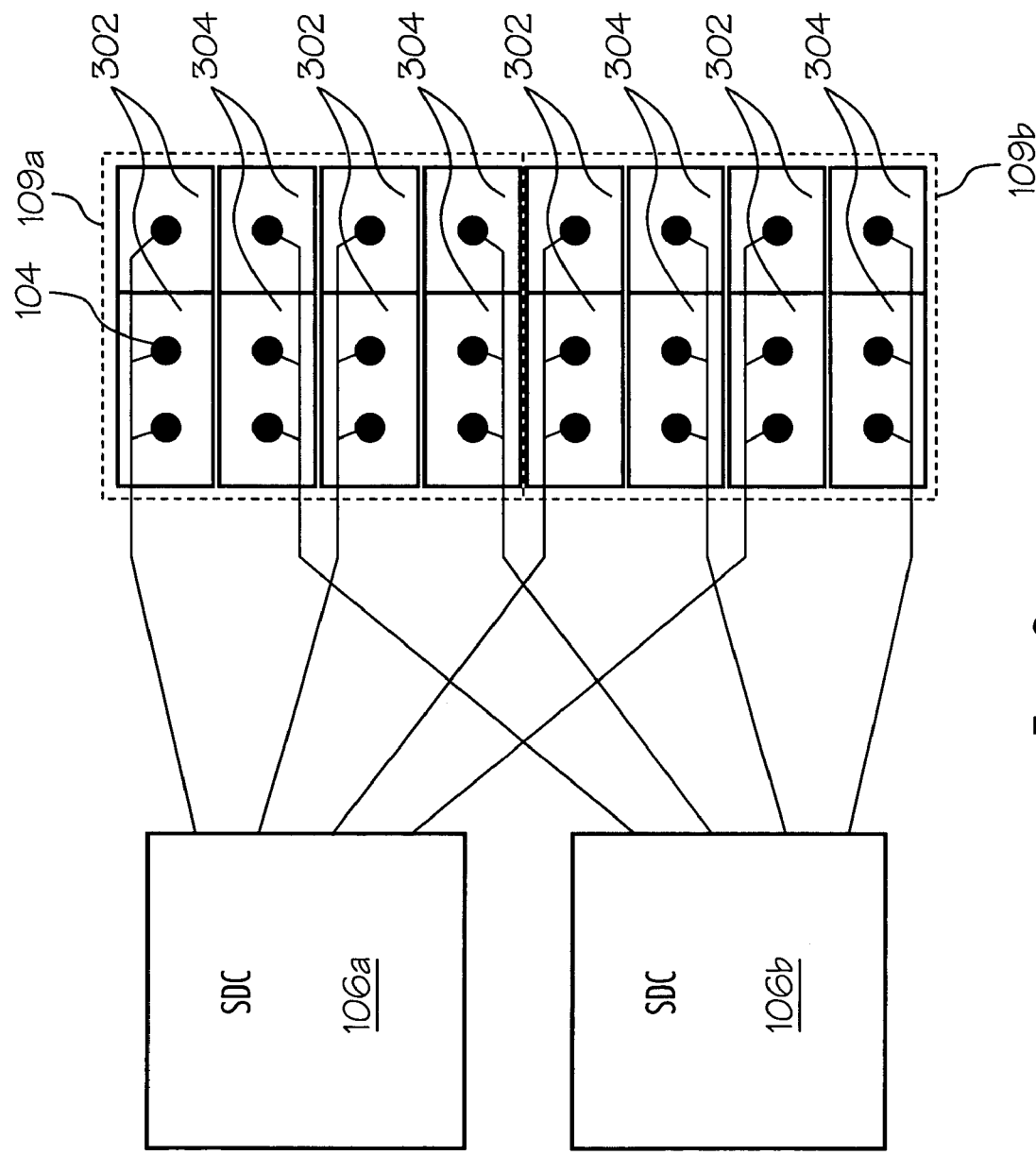
FIG. 3 illustrates an embodiment of a sensor distribution method to couple sensors to sensor data collectors system in accordance with the teachings of the present invention.

FIG. 3 illustrates an exemplary sensor 104 and SDC 106 arrangement that enhances the availability of a system 100 in accordance with the teachings of the present invention. FIG. 3 illustrates part of the structure seen in FIG. 2. In a first exemplary embodiment, as shown in FIG. 3, the sensors 104 are coupled to two different SDCs 106a-106b in an alternating fashion such that the sensors 104 of a specific zone 109 are split between at least two SDCs 106a-106b. As illustrated in FIG. 3, the sensors 104 in first sections 302 are associated with a first SDC 106a and the sensors 104 in second sections 304 are associated with a second SDC 106b. Note that in this arrangement, sensors 104 which occupy one zone (such as zone 109a) are now coupled to one of two SDCs; either first SDC 106a (for first sections 302) or second SDC 106b (for second section 304). Thus, if one SDC failed, such as first SDC 106a, nondestructive testing could still be done in zone 109a using the sensors 104 associated with SDC 106b. While a particular pattern is illustrated in FIG. 3, the exact arrangement of sensors 104 and sensor sections can be altered within the scope of the present invention.

Figure 4:
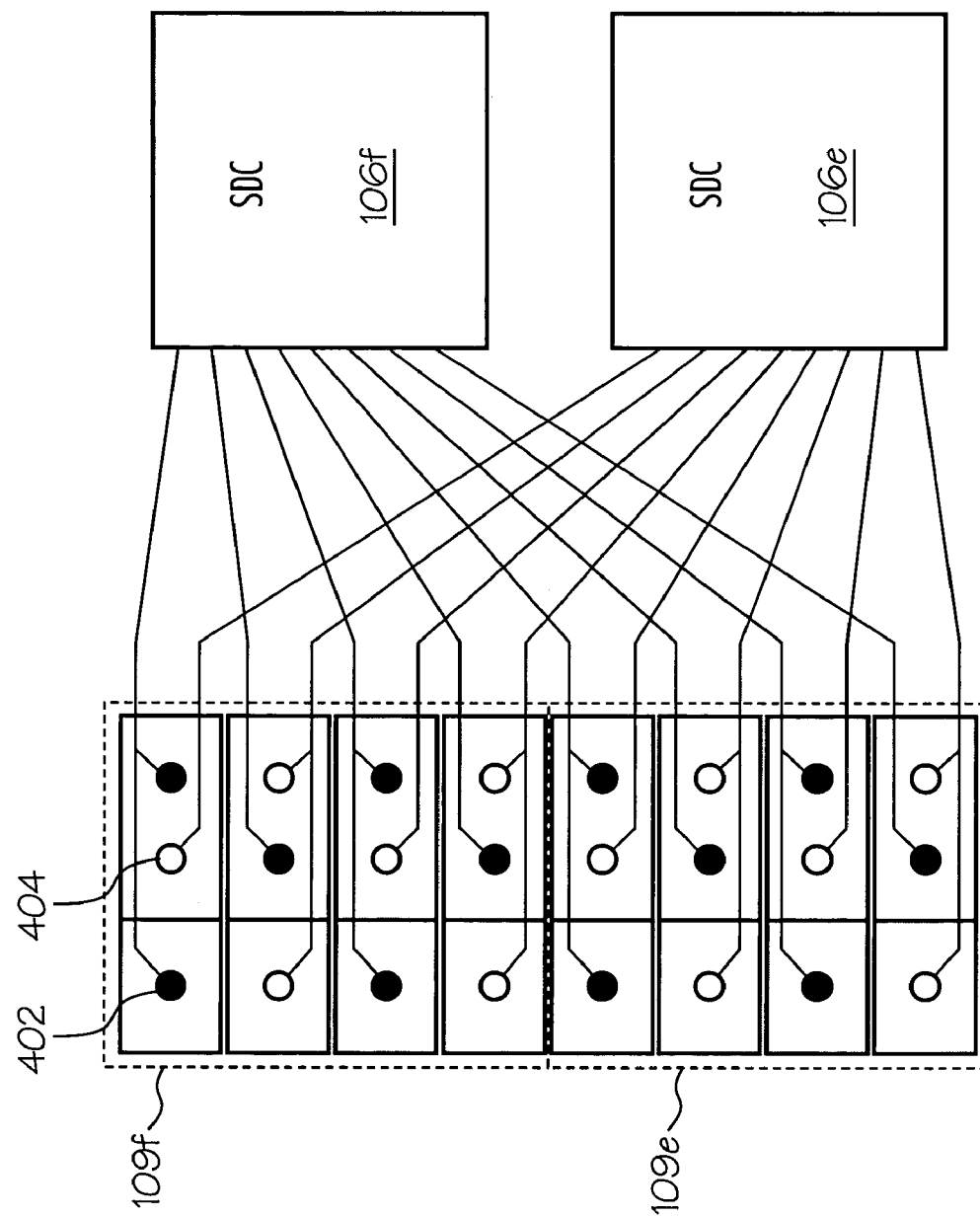
FIG. 4 illustrates another embodiment of a sensor distribution method to couple sensors to sensor data collectors system in accordance with the teachings of the present invention.

A second embodiment of an exemplary arrangement that enhances availability of the system 100 is illustrated in FIG. 4. In accordance with the teachings of the present invention, the sensors 104 in zone 109 are divided into two groups with a first group of sensors 104 associated with a SDC 106 and a second group of sensors 104 associated with another SDC 106. For example, as seen in zone 109e and 109f of FIG. 4, first sensors 402 are associated with sixth SDC 106f and second sensors 404 (represented as open circles in FIG. 4) are associated with fifth SDC 106e. Note again that in this arrangement, sensors 104, which occupy one zone (such as zone 109e) are now coupled to one of two SDCs; either fifth SDC 106e (for second sensors 404) or sixth SDC 106f (for first sensors 402). Thus, if one SDC failed, such as fifth SDC 106e, nondestructive testing could still be done in zone 109e using the sensors associated with sixth SDC 106f. While a number of sensors and a particular pattern of sensors are illustrated in FIG. 4, the exact arrangement of sensors can be altered within the scope of the present invention. Additionally, while an even distribution of sensors is shown, the division of sensors does not have to be even and the sensors in a zone 109 can be divided between more than two SDCs.

Figure 5:
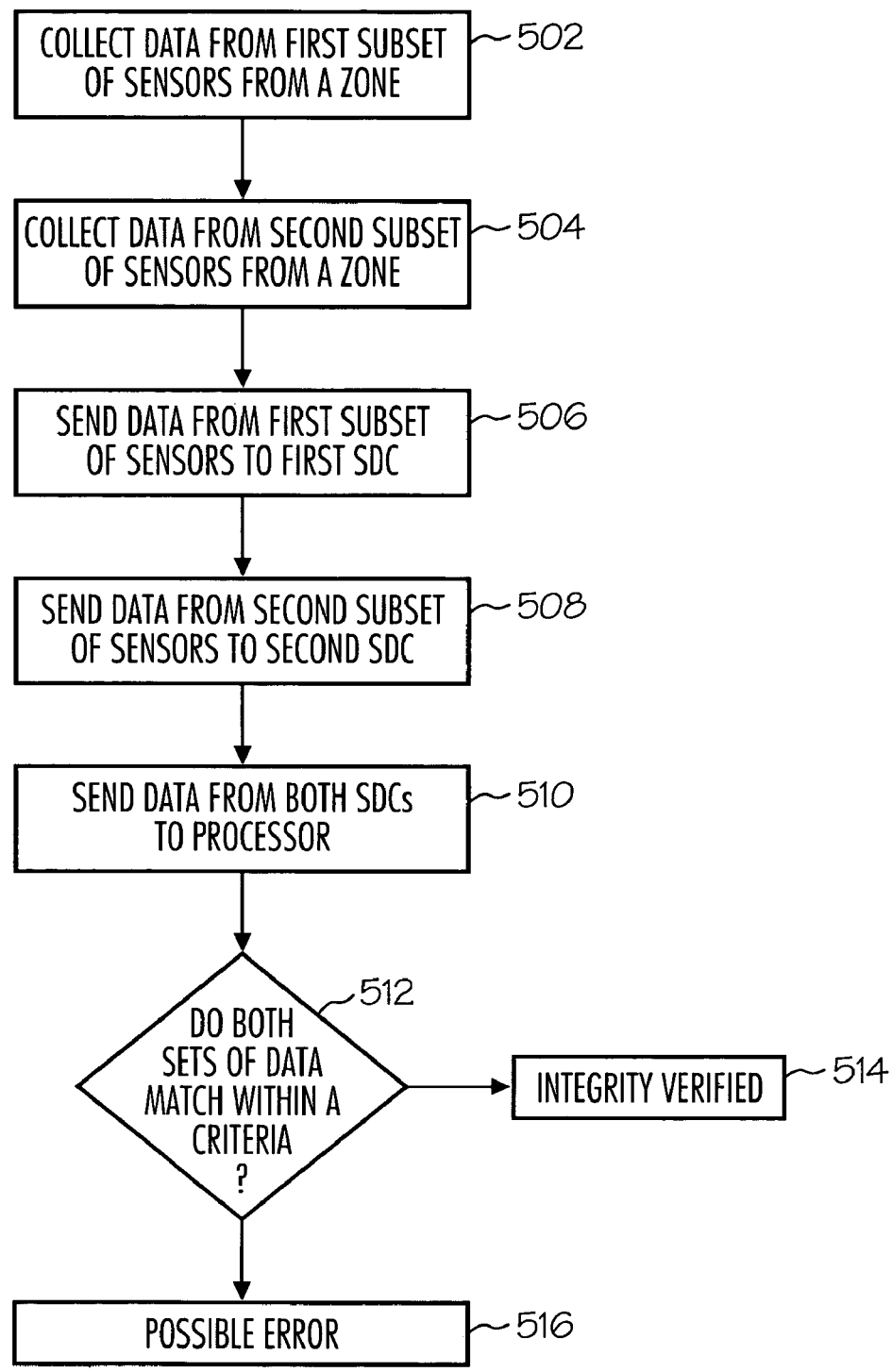
FIG. 5 is a flowchart of a method for operating a structural health monitoring system in accordance with the teachings of the present invention.

Another benefit of distributing sensors 104 from one zone 109 between multiple SDCs 106 is that such a distribution allows for a method to check the integrity of the system 100. FIG. 5 is a flowchart illustrating a method to check the integrity of a structural health management system in accordance with the teachings of the present invention.

In a first step, 502, data is collected from a first subset of sensors 104 from a zone 109. As discussed previously, in one embodiment, the data collected is in the form of electrical signals containing information regarding the structural health of the tested material. The waves are created by ultrasonic pulses generated by the sensors 104. The electrical signals are produced by sensors by converting echoes and received waves produced by the reflection of waves off of structure internal to the tested material. In a second step, 504, data is collected from a second subset of sensors 104 from the same zone 109. Preferably, the first subset and the second subset of sensors 104 are different sensors from the zone 109. The combination of the first subset and the second subset does not necessarily equal the set of all sensors in the zone 109.

The data collected by the first subset of sensors 104 is sent to a first sensor data collector (SDC) 106 in step 506. The data collected by the second subset of sensors 104 is sent to a second SDC 106 in step 508. As discussed previously, by splitting the output of the sensors 104 from a zone 109 between two or more SDCs 106, the availability of the system is enhanced because the loss of a SDC 106 would not result in the loss of the ability to perform testing in an entire zone 109 because at least a portion of the sensors from the zone 109 would still be coupled to a working sensor data collector 106.

Next, the data from the first sensor data collector and the second sensor data collector are sent to a processor 108 in step 510. The processor 108, in step 512, can then compare the data collected by the first sensor data collector and the second sensor data collector to determine the similarity between the data. In one embodiment, the comparison is done after the data is processed to extract a relevant data set that can be compared. This processing can be done at the processor 108, at the SDC 106 or at split between the SDC 106 and the processor 108. Because the data is from the same zone 109, and the structure for that zone 109 does not change during testing, the data and the result of the data from both the first subset of sensors and the second subset of sensors should be similar. If the first subset of sensors and the second subset of sensors are a match within a predetermined margin or criteria then the integrity of the system is verified in step 514.

However, if the data from the first subset does not match the data from the second subset, in step 516 a warning is issued that there could be an error in the sensors, in the sensor data collectors or in the connections between the sensors and the sensor data collectors. This comparison can therefore help avoid misleading test results. While the method of FIG. 5 is discussed with reference to an embodiment where the sensors 101 from one zone 109 is distributed between two SDCs 106, the sensors 104 can be distributed between more than two SDCs 106.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

The invention claimed is:

1. A method for operating a structural health management system comprising:
    gathering data from a first zone of sensors and a second zone of sensors, each of the sensors mounted on a test material;
    sending data from at least a first subset of sensors of the first zone of sensors to a first sensor data collector;
    sending data from at least a first subset of sensors of the second zone of sensors to the first sensor data collector;
    sending data from a second subset of sensors of the first zone of sensors to a second sensor data collector;
    sending data from the first subset of sensors of the first zone to a processor from the first sensor data collector;
    sending data from the second subset of sensors of the first zone to the processor from the second sensor data collector;
    comparing the data from the first sensor data collector and the second sensor data collector; and
    indicating a possible error condition indicative of a defective sensor if the data from the first sensor data collector and the data from the second sensor data collector differ by a predetermined amount.

2. The method of claim 1,
    further comprising storing the data from the first and second sensor data collectors in a memory associated with the processor.

3. The method of claim 1 wherein the step of gathering data comprises:
    generating elastic waves in the test material by pulsing each sensor;
    receiving the elastic waves, the received elastic waves potentially altered by formations internal to the material; and
    converting the received elastic waves to electrical signals representative of the structural health of the test material.

4. The method of claim 3 wherein the step of generating elastic waves in the test material comprises generating an elastic wave in an aircraft skin.

5. A method operating a structural health monitoring system comprising:
    sending signals from a first subset of a zone of sensors to a first sensor data collector;
    sending signals from a second subset of the zone of sensors to a second sensor data collector;
    sending the signals from the first sensor data collector and the second data collector to a processor; and
    evaluating the signals using the processor.

6. The method of claim 5 further comprising the steps of:
    generating elastic waves in the test material by pulsing each sensor;
    receiving the elastic waves, the received elastic waves altered by formations internal to the material; and
    converting the received elastic waves to electrical signals representative of the structural health of the test material.

7. The method of claim 6 wherein the step of generating elastic waves in the test material comprises generating a wave in an aircraft skin.

8. The method of claim 5 further comprising:
    comparing the signals from the first subset and the second subset in the processor; and
    indicating a potential fault in the system if the first subset of signals and the second subset of signals differ by a predetermined threshold.

9. The method of claim 5 further comprising collecting data from the first subset in the first sensor data collector upon detection of a failure of the second sensor data collector.

10. A structural health management system comprising:
    a plurality of sensors mounted on a structure, the plurality of sensors arranged in two or more zones;
    a plurality of sensor data collectors comprising a first sensor data collector and a second sensor data collector, each sensor data collector coupled to sensors from at least two zones, wherein a first subset of sensors in a first zone is coupled to the first sensor data collector of the one or more sensor data collectors and a second subset of sensors in the first zone is coupled to the second sensor data collector of the one or more sensor data collectors; and
    a processor coupled to each of the one or more sensor data collectors, the processor operable to receive data from each of the one or more sensor data collectors and perform a damage assessment.

11. The system of claim 10 wherein each of the plurality sensors is an ultrasonic transducer for use in ultrasonic testing.

12. The system of claim 10 wherein the structure is a section of an aircraft.

13. The system of claim 11 wherein the data associated with each of the sensors includes data collected in an ultrasonic test, and each of the sensors sends the data from the ultrasonic test via the sensor data collectors to the processor coupled to the sensor data collectors, the processor configured to analyze the data from the ultrasonic test to locate flaws in the structure.

14. The system of claim 13 wherein the processor is further operable to compare a first set of data from the first zone coupled to a first sensor data collector and the second set of data from the first zone coupled to the second sensor data collector and signal an error condition if the first set of data and the second set of data vary by a predetermined amount.

15. A structural health management system comprising:
    a plurality of sensors mounted on a structure, the plurality of sensors arranged in two or more zones;
    a first sensor data collector and a second sensor data collector, each coupled to sensors from at least two zones, wherein a first subset and a second subset of sensors in a first zone are coupled to the first sensor data collector and a first subset and a second subset of sensors in a second zone are coupled to the second sensor data collector; and a processor coupled to the sensor data collector, the processor operable to receive data from the sensor data collector and perform a damage assessment.

16. The system of claim 15 wherein each of the plurality sensors is an ultrasonic transducer for use in ultrasonic testing.

17. The system of claim 15 wherein the structure is a section of an aircraft.

18. The system of claim 16 wherein the data associated with each of the plurality of sensors includes data collected in an ultrasonic test, and each of the plurality of sensors sends the data from the ultrasonic test via the sensor data collectors to the processor coupled to the sensor data collectors, the processor configured to analyze the data from the ultrasonic test to locate flaws in the structure.

19. A structural health monitoring system comprising;
a plurality of sensors distributed as two or more zones of sensors mounted on a structure, the sensors configured to collect data;
a plurality of sensor data collectors, each coupled to a subset of the sensors from at least two of the two or more zones of sensors, the sensor data collectors configured to receive data from the subset of sensors to which it is coupled; and
a processor coupled to the sensor data collector, the processor configured to receive and evaluate data from the sensor data collector.

20. The system of claim 19 wherein the structural health monitoring system further comprises one or more sensors from a first zone of sensors coupled to a first sensor data collector and one or more sensors from a second zone of sensors coupled to the first sensor data collector.

21. The system of claim 19 wherein the structural health monitoring system further comprises a plurality of sensors of a first zone of sensors coupled to two or more sensor data collectors.

22. The system of claim 19 wherein the structural health monitoring system further comprises a first portion of sensors from a first zone of sensors coupled to a first sensor data collector and a second portion of sensors from the first zone of sensors coupled to a second sensor data collector.

23. The system of claim 22 wherein:
the first portion of sensors collects a first set of data regarding the structure;
the second portion of sensors collects a second set of data regarding the structure;
the first sensor data collector receives the first set of data from the first portion of sensors;
the second sensor data collector receives the second set of data from the second portion of sensors; and
the processor receives the first set of data and the second set of data, the processor analyzes the first and second data to determine if the first set of data and the second set of data match within a predetermined criteria, wherein a match verifies the integrity of the system.

24. The system of claim 19 wherein the structural health monitoring system further comprises a first portion of sensors from a first zone of sensors coupled to a first sensor data collector and a second portion from the first zone of sensors coupled to a second sensor data collector.

25. The system of claim 22 wherein the second sensor data collector sends data from the second portion of sensor from the first zone of sensors to a processor upon failure of the first sensor data collector.

26. The system of claim 19 wherein the sensors are ultrasonic transducers configured to perform ultrasonic tests upon the structure.

27. The system of claim 26 where in the structure is an aircraft skin.

28. The system of claim 19 wherein the structure is an aircraft skin.

29. The system of claim 28 wherein the sensors are ultrasonic transducers configured to produce lamb waves with in the aircraft skin and receive signals indicative of internal structures and flaws within the aircraft skin.

30. The method of claim 5 further comprising the step of:
storing the signals from the first subset of the zone of sensors, the signals from the second subset of the zone of sensors, or the signals from both the first and second subsets of the zone of sensors in a memory.

31. The system of claim 10 further comprising a memory coupled to processor, the memory configured to store the data from each of the sensor data collectors.

32. The system of claim 15 further comprising a memory coupled to processor, the memory configured to store the data from the sensor data collector.

33. The system of claim 19 further comprising a memory coupled to processor, the memory configured to store the data from the sensor data collectors.

* * * * *